(12) United States Patent
Garcia et al.

(10) Patent No.: US 9,364,402 B1
(45) Date of Patent: Jun. 14, 2016

(54) ANALGESIC CLEANSING COMPOSITION

(71) Applicant: The Dial Corporation, Phoenix, AZ (US)

(72) Inventors: Gabriel Garcia, Phoenix, AZ (US); Catherine Schmit, Glendale, AZ (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

(21) Appl. No.: 14/587,950

(22) Filed: Dec. 31, 2014

Related U.S. Application Data

(63) Continuation-in-part of application No. 14/587,414, filed on Dec. 31, 2014.

(51) Int. Cl.
| | |
|---|---|
| *A61K 8/02* | (2006.01) |
| *A61K 38/00* | (2006.01) |
| *A61K 31/045* | (2006.01) |
| *A61K 8/37* | (2006.01) |
| *A61K 31/618* | (2006.01) |
| *A61K 8/11* | (2006.01) |
| *A61Q 19/10* | (2006.01) |

(52) U.S. Cl.
CPC ... *A61K 8/37* (2013.01); *A61K 8/11* (2013.01); *A61K 31/618* (2013.01); *A61Q 19/10* (2013.01)

(58) Field of Classification Search
None
See application file for complete search history.

(56) References Cited

U.S. PATENT DOCUMENTS

| 4,511,563 A | 4/1985 | Schmolka | |
|---|---|---|---|
| 7,037,513 B1 | 5/2006 | Traynor et al. | |
| 2006/0110415 A1* | 5/2006 | Gupta | A61K 8/0212 424/401 |
| 2006/0292245 A1 | 12/2006 | Schmit et al. | |
| 2008/0139507 A1* | 6/2008 | Gupta | A61K 8/26 514/63 |
| 2011/0244030 A1* | 10/2011 | Lebel | 424/450 |
| 2014/0127320 A1* | 5/2014 | Salamone et al. | 424/618 |

FOREIGN PATENT DOCUMENTS

JP    07-215848 A    8/1995

OTHER PUBLICATIONS

Handbook of Pharmaceutical Excipients (1998); p. 253 (silica).*
PCT International Search Report (PCT/US2015/066559) dated Apr. 29, 2016.

* cited by examiner

*Primary Examiner* — Jeffrey T Palenik
(74) *Attorney, Agent, or Firm* — David K. Benson

(57) ABSTRACT

Composition and methods are provided for analgesic cleansing compositions, which may be either wash-off or leave-on cleansing compositions. Such compositions comprise a number of surfactants and a number of analgesic compounds, and may optionally comprise antibacterial agents and/or a cosmetically suitable carrier. A method of making an analgesic soap composition is also provided. A method of using a wash-off analgesic cleansing composition is also provided.

16 Claims, 3 Drawing Sheets

ANALGESIC CLEANSING COMPOSITION

CROSS-REFERENCES TO RELATED APPLICATIONS

This is a continuation-in-part of application Ser. No. 14/587,414, filed Dec. 31, 2014, the entire contents and substance of which are hereby incorporated in total by reference.

FIELD OF THE INVENTION

The present invention generally relates to cleansing compositions, and more particularly relates to the incorporation of topical analgesics in cleansing compositions. The present invention also relates to a method of incorporating a topical analgesic into a soap preparation.

BACKGROUND OF THE INVENTION

Humans have been making soap since at least the times of ancient Babylon. In the almost five millennia since humans started making soap, the soap has taken a variety of forms and been used for a variety of purposes, most of which have been cleansing compositions.

Hand sanitizer compositions have been developed which have antibacterial properties, and which are able to cleanse the hands without the need for direct contact with water. Such hand sanitizers may be alcohol- or water-based compositions, and allow a user to cleanse their hands without the dehydrating effects on the skin that have been associated with wash-off cleansing compositions because such sanitizing compositions leave the natural oils on the skin intact.

Soap bars are cleansing compositions that are in solid form and as a consequence, do not require containers, cannot be spilled, and are used incrementally. During use, an outer layer of a soap bar is removed while leaving the layers underneath unaffected.

Liquid cleansing compositions—including liquid soaps—have gained much popularity because the liquid form of the soap may allow incorporation of a number of additive ingredients that improve the rheological properties, antibacterial efficacy, foam generation and other properties which cause liquid soaps to appeal to consumers. Liquid cleansing compositions may be provided in dispensers which may provide a consumer with the impression that the liquid cleansing composition is not readily contaminated.

Accordingly, it is desirable to provide a cleansing composition that may be used to cleanse a skin surface. In addition, it is desirable to provide a cleansing composition that has additional utility. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A cleansing composition is provided for cleansing the skin simultaneously with providing analgesic benefits to the subdermal tissue. The analgesic cleansing composition includes a cosmetically suitable carrier, at least one surfactant, and at least one analgesic compound to alleviate pain in a user. The analgesic cleansing composition is a liquid, and is also a leave-on cleansing composition.

A method is provided for producing a cleansing composition which contains an analgesic compound. The method includes combining at least one anionic surfactant with an analgesic composition and a cosmetically suitable carrier to create a mixture. The analgesic composition includes at least one topical analgesic compound. The method also includes mixing the mixture to homogeneity to create an analgesic cleansing composition. The analgesic cleansing composition contains a sufficient amount of the at least one topical analgesic compound to provide analgesia upon contact with skin.

A consumer product is provided to simultaneously cleanse the skin and relieve muscle pain. The consumer product includes a cosmetically suitable carrier, at least one surfactant to cleanse the skin, and at least one analgesic compound to alleviate muscle pain in a user. The consumer product is a liquid, is contained in a vessel capable of dispensing the consumer product, and is also a leave-on cleansing composition.

BRIEF DESCRIPTION OF THE DRAWINGS

The present invention will hereinafter be described in conjunction with the following drawing figures, wherein like numerals denote like elements.

DETAILED DESCRIPTION OF THE INVENTION

Figure 1:
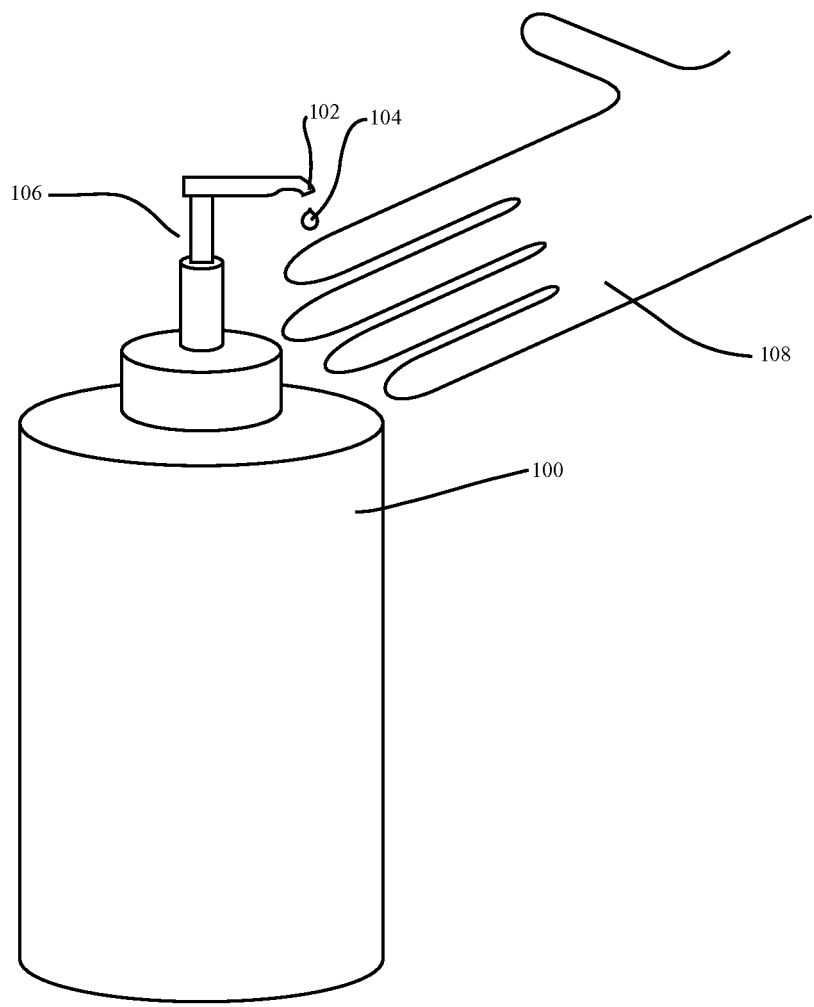
FIG. 1 is a diagram of a container dispensing an analgesic skin cleansing composition, according to an example of the principles described herein.

The following detailed description of the invention is merely exemplary in nature and is not intended to limit the invention or the application and uses of the invention. Furthermore, there is no intention to be bound by any theory presented in the preceding background of the invention or the following detailed description of the invention.

As mentioned above, cleansing compositions such as soaps and hand sanitizers are used by individuals to cleanse or otherwise sanitize their skin. Topical analgesic compositions have also been used to provide relief from muscle and ligament soreness. However, topical analgesics have been presumed to be slow-acting compounds, and the efficacy of such compounds is based on the diffusion of the active component across skin and into the underlying tissues. Existing topical analgesic compositions are applied as leave-on creams or gels, in order to allow more extended contact between the skin and the analgesic compound than a wash-off composition would allow. Such extended contact allows the analgesic compound to diffuse across the skin and access the site of action, which may be underneath the skin.

Accordingly, the present specification is directed to combining analgesic benefits with cleansing compositions. These compositions may take the form of a leave-on composition, and may also take the form of a wash-off composition. The present specification is directed to the surprising discovery that analgesic compounds can be made effective even with a very short contact period, such as that which would be expected of a wash-off cleansing composition, or with a leave-on cleansing composition prior to evaporation of the cosmetically suitable carrier.

More specifically, a wash-off cleansing composition may contain at least one surfactant, which enables the wash-off cleansing composition to be used to cleanse the skin of a user. A wash-off cleansing composition may also contain at least one analgesic compound, which enables the wash-off cleansing composition to be used to relieve muscle pain of a user.

For individuals leading an active lifestyle, aches and pains may be frequently experienced, and may even be an accepted facet of such an active lifestyle. A number of products may exist which are applied as leave-on compositions to the surface of the skin to relieve muscle pain; such products contain analgesic compounds as active agents. The analgesic compounds may be selected so that they diffuse through the skin, and thus reach the site of action and achieve the desired analgesic effect.

The present specification is directed to the surprising discovery that analgesic compounds may be delivered in effective quantities in a leave-on cleansing composition which is applied to the surface of the skin. Previous work with topical analgesic compounds has not included their use in cleansing compositions. The cosmetically suitable carrier of topical analgesic compositions serves to hold the topical analgesic compound in close proximity to the skin in order to promote diffusion through the skin over an extended contact period. Accordingly, the present specification is directed to the surprising discovery that analgesic compounds may be delivered in effective quantities in the brief duration prior to evaporation of the cosmetically suitable carrier of a leave-on cleansing composition. Similarly, while leave-on cleansing compositions may produce a cooling effect due to the evaporation of the cosmetically suitable carrier, these compositions have not been able to provide fast or effective analgesia to the underlying tissues.

Cleansing compositions according to the present specification may be provided in a variety of forms. For example, liquid surfactant compositions may be one type of cleansing composition. As another example, solid surfactant compositions, such as bar soaps, may be another type of cleansing composition.

Surfactants may be included in the cleansing composition. A cleansing composition according to the present specification may also have analgesic properties, and may include at least one analgesic compound. An analgesic cleansing composition according to the present specification may also contain a number of other additives, which will be discussed in greater detail below.

An analgesic cleansing composition according to the present specification may include at least one surfactant. A surfactant may have a hydrophobic end and a hydrophilic end. The hydrophobic end may allow the surfactant to interact with uncharged molecules, such as oils. The hydrophilic end may facilitate the interaction of the molecule with charged or polar molecules, such as water. The hydrophilic end may be used to classify surfactants, which may be anionic, cationic, nonionic, amphoteric, or zwitterionic. Anionic surfactants may have a negatively charged hydrophilic end. Examples of anionic surfactants include sulfate, sulfonate, carboxylate, phosphate, or the like. Anionic surfactants may be sensitive to water hardness. Cationic surfactants may be those that have a positively charged hydrophilic end, such as a quaternary amine. Nonionic surfactants may have a hydrophilic end which may be charge neutral, such as an ethoxylate, glycoside, or poly-ol; such surfactants may not be sensitive to water hardness. Amphoteric surfactants may be those that have a hydrophilic end which has a functional group that is capable of acting as a base, and a functional group that is capable of acting as an acid, such as amine oxides. Zwitterionic surfactants may have both a positive and negative charge on their hydrophilic ends, such as sultaines, or betaines. The hydrophobic end may include a saturated or unsaturated, linear or branched, substituted or unsubstituted, cyclic or acyclic alkyl chain containing at least 8 carbon atoms.

For the purposes of the present specification, "alkyl" may refer to saturated or unsaturated, branched or unbranched, cyclic or acyclic, substituted or unsubstituted hydrocarbon chains of any length. For example, alkyl may refer to saturated hydrocarbon chains, such as lauryl groups ($-C_{12}H_{25}$), myristyl groups ($-C_{14}H_{29}$), cetyl groups ($-C_{16}H_{33}$), stearyl groups ($-C_{18}H_{37}$), isostearyl groups ($-C_{18}H_{37}$), and the like. In another example, alkyl may refer to unsaturated hydrocarbon chains, such as oleyl groups ($-C_{18}H_{35}$), linoleyl groups ($-C_{18}H_{33}$), and the like. In a further example, alkyl may refer to hydrocarbons bearing additional heteroatom substituents, such as ricinoleyl groups ($-C_{18}H_{35}O$), and the like. In a still further example, alkyl may refer to hydrocarbons bearing cyclic groups, which may optionally contain heteroatoms, such as dodecylbenzyl groups ($-C_{18}H_{29}$), dodecylpyridinyl groups ($-C_{17}H_{29}N$), and the like.

Anionic surfactants may include alkyl carboxylic acids, alkyl ether carboxylic acids, alkyl phosphates, alkyl ether phosphates, alkyl sulfates, alkyl ether sulfates, alkyl sulfonates, alkyl ether sulfonates, and salts thereof. In principle, any type, number, or combination of anionic surfactants may be used in compositions according to the present specification; selected examples are provided below.

A soap may be included as an ingredient in the cleansing composition. A soap may be a salt of an alkyl carboxylic acid. For example, a soap may be an ammonia, alkali or alkaline earth metal salt of a fatty carboxylic acid. A soap that is an alkaline earth metal salt may be either a divalent salt of two fatty acid chains or a single fatty acid chain and another anion, for example a hydroxide ion ($^-OH$).

Suitable non-limiting examples of soaps which may be used according to the present specification include sodium, potassium or lithium salts of caprylic acid, capric acid, lauric acid, myristic acid, palmitic acid, stearic acid, arachidic acid, behenic acid, lignoceric acid, cerotic acid, oleic acid, myristoleic acid, palmitoleic acid, sapienic acid, elaidic acid, vaccenic acid, linoleic acid, linolenic acid, isostearic acid, ricinoleic acid, hydroxystearic acid, and dihydroxystearic acid.

Additional non-limiting examples of soaps which may be used according to the present specification include soaps which are prepared by saponification of triglycerides and that are not purified to homogeneity. Such soaps may include, for example, sodium, potassium and lithium soaps made from coconut oil, olive oil, rapeseed oil, castor oil, shea butter, cocoa butter, palm oil, and avocado oil.

Soaps may be included in analgesic cleansing compositions according to the present specification in concentrations ranging from 0% to 95% by weight, relative to the total weight of the composition. For example, a soap may be included in the analgesic cleansing composition according to the present specification at a concentration ranging from 30% to 90%. In another example, the analgesic cleansing composition according to the present specification may contain a soap at a concentration ranging from 45% to 85%. In a further example, a concentration of soap ranging from 55% to 80% may be used in compositions according to the present specification. In a still further example, a soap concentration ranging from 65% to 75% may be used in compositions according to the present specification. In another example, soaps may be included in the analgesic cleansing composition according to the present specification in concentrations ranging from 5% to 95% by weight, relative to the total weight of the composition. In another example, soaps may be included in the analgesic cleansing composition according to the present specification at concentrations ranging from 4% to 10% by weight, relative to the total weight of the composition. All of the above concentrations are provided as percentages by weight, relative to the total weight of the composition.

Another type of anionic surfactant which may be used according to an example of the present specification is an alkyl carboxylic acid type of surfactant. Alkyl carboxylic acids may be fatty acids which are provided in the protonated (acid) form. Suitable non-limiting examples of alkyl carboxylic acids are the soaps noted above when provided in the acid form.

Another type of anionic surfactant which may be used according to an example of the present specification include alkyl sulfates. Alkyl sulfates may also be used according to the present specification as salts of ammonia, alkali or alkaline earth metals.

Suitable non-limiting examples of alkyl sulfates which may be used according to an example of the present specification include lauryl sulfate, myristyl sulfate, cetyl sulfate, stearyl sulfate, oleyl sulfate, linoleyl sulfate, isostearyl sulfate, ricinoleyl sulfate, behenyl sulfate, and salts and/or mixtures thereof. For example, sodium, potassium or ammonium salts of the above alkyl sulfates may be used.

Another type of anionic surfactant which may be used according to an example of the present specification include an alkyl ether sulfate type of surfactant, which may be surface-active agents which contain an ether linkage separating the alkyl group from the sulfate group. In principle, any ether linkage of a diol or polyol may be used. For example, ethylene or polyethylene glycol ether linkages may be used. In another example, propylene or polypropylene glycol ethers may be used. In a further example, glyceryl or polyglyceryl ether linkages may be used. In a still further example, butylene or polybutylene glycol ethers may be used. Alkyl ether sulfates may be provided in either the protonated form or as salts of ammonia, alkali or alkaline earth metals.

Suitable non-limiting examples of alkyl ether sulfates which may be used according to an example of the present specification include laureth-2 sulfate, laureth-3 sulfate, laureth-5 sulfate, laureth-6 sulfate, laureth-10 sulfate, laureth-12 sulfate, myristyl-2 sulfate, myristyl-5 sulfate, myristyl-10 sulfate, cetyl-2 sulfate, cetyl-4 sulfate, cetyl-6 sulfate, cetyl-10 sulfate, stearyl-2 sulfate, stearyl-3 sulfate, stearyl-4 sulfate, stearyl-12 sulfate, and mixtures and/or salts thereof.

Another type of anionic surfactant which may be used according to an example of the present specification is an alkyl ether carboxylic acid type of surfactant. Alkyl ether carboxylic acids may be surface-active agents which have a carboxylic group as the hydrophilic group, and an ether linkage between the carboxylic acid group and the alkyl chain. In principle, any ether linkage of a diol or polyol may be used. For example, ethylene or polyethylene glycol ether linkages may be used. In another example, propylene or polypropylene glycol ethers may be used. In a further example, glyceryl or polyglyceryl ether linkages may be used. In a still further example, butylene or polybutylene glycol ethers may be used. Alkyl ether carboxylic acids may be provided in either the protonated (acid) form, or as salts of ammonia, alkali or alkaline earth metals.

Suitable non-limiting examples of alkyl ether carboxylic acids include butoxynol-5 carboxylic acid, butoxynol-19 carboxylic acid, capryleth-2 carboxylic acid, capryleth-4 carboxylic acid, capryleth-6 carboxylic acid, capryleth-9 carboxylic acid, ceteareth-2 carboxylic acid, ceteareth-10 carboxylic acid, ceteareth-25 carboxylic acid, coceth-7 carboxylic acid, laureth-2 carboxylic acid, laureth-3 carboxylic acid, laureth-4 carboxylic acid, laureth-5 carboxylic acid, laureth-6 carboxylic acid, laureth-7 carboxylic acid, laureth-8 carboxylic acid, laureth-10 carboxylic acid, laureth-11 carboxylic acid, laureth-20 carboxylic acid, myreth-2 carboxylic acid, myreth-3 carboxylic acid, myreth-4 carboxylic acid, myreth-5 carboxylic acid, myreth-6 carboxylic acid, steareth-2 carboxylic acid, steareth-3 carboxylic acid, steareth-4 carboxylic acid, steareth-5 carboxylic acid, steareth-6 carboxylic acid, oleth-2 carboxylic acid, oleth-4 carboxylic acid, oleth-10 carboxylic acid, and mixtures and/or salts thereof.

Another type of anionic surfactant which may be used according to an example of the present specification is an alkyl sulfonate type of surfactant. Alkyl sulfonates may be surface-active agents which have an alkyl group directed linked to the sulfur of the sulfonate group. Alkyl sulfonates may also be provided as salts of ammonia, alkali or alkaline earth metals.

Suitable non-limiting examples of alkyl sulfonate type surfactants which may be used in accordance with an example of the present specification include dodecylbenzenesulfonate, C13-17 alkane sulfonate, C14-18 alkane sulfonate, cocoamphohydroxypropylsulfonate, C12-14 olefin sulfonate, C14-16 olefin sulfonate, C16-18 olefin sulfonate, and mixtures and/or salts thereof.

Another type of anionic surfactant which may be used according to an example of the present specification is an alkyl phosphate type of surfactant. Alkyl phosphates may be surfactants bearing a phosphate group as the hydrophilic group, and may contain one or more alkyl groups. Alkyl phosphates may be provided in either the protonated form or as an ammonia, alkali or alkaline earth metal salt.

Suitable non-limiting examples of alkyl phosphate surfactants which may be used in accordance with an example of the present specification include phospholipid EFA (linoleamidopropyl PG-dimonium chloride phosphate), phospholipid PTC (cocamidopropyl PG-dimonium chloride phosphate), phospholipid CDM (sodium coco PG-dimonium chloride phosphate), phospholipid SV (stearamidopropyl PG-dimonium chloride phosphate), phospholipid GLA (sodium borageamidopropyl PG-dimonium chloride phosphate), lauryl phosphate, dilauryl phosphate, myristyl phosphate, dimyristyl phosphate, cetyl phosphate, dicetyl phosphate, stearyl phosphate, distearyl phosphate, behenyl phosphate, dibehenyl phosphate, oleyl phosphate, dioleyl phosphate, and salts and/or mixtures thereof.

Another type of anionic surfactant which may be used according to an example of the present specification is an alkyl ether phosphate type of surfactant. Alkyl ether phosphates may be surface-active agents bearing an ether linkage between one or more alkyl groups and the phosphate group. In principle, any ether linkage of a diol or polyol may be used. For example, ethylene or polyethylene glycol ether linkages may be used. In another example, propylene or polypropylene glycol ethers may be used. In a further example, glyceryl or polyglyceryl ether linkages may be used. In a still further example, butylene or polybutylene glycol ethers may be used. Alkyl ether phosphates may be provided in either their protonated form or as an ammonia, alkali or alkaline earth metal salt.

Suitable non-limiting examples of alkyl ether phosphates include PPG-5-ceteth-10 phosphate, oleth-3 phosphate, oleth-10 phosphate, and mixtures and/or salts thereof.

Anionic surfactants may be included in compositions according to the present specification separately from soaps, and may be included in amounts ranging from 0% to 50% by weight. For example, concentrations of the anionic surfactants other than soaps may range from 1% to 20%. Still further concentrations of the anionic surfactants other than soaps may range from 1.5% to 10%. All concentrations are provided as a percentage by weight, relative to the total weight of the composition.

Compositions according to an example of the present specification may also contain nonionic surfactants. For example, the composition may include alkoxylated fatty alcohols, alkoxylated fatty esters, alkanolamides, alkyl glycosides, and combinations thereof.

Alkoxylated fatty alcohols may be incorporated in compositions according to the present specification as a nonionic surfactant. Alkoxylated fatty alcohols may be condensation products of a number of alkoxy groups with a fatty alcohol. In principle, any type or number of alkoxy groups may be used. For example, ethylene glycol or polyethylene glycol, propylene or polypropylene glycol, glyceryl or polyglyceryl, butylene or polybutylene glycol may be used. In a further example, combinations of the above may be used, such as a combination of polyethylene glycol and polypropylene glycol, as either a random- or block-condensation product.

Suitable non-limiting examples of alkoxylated fatty alcohols for use in compositions according to the present specification are ceteth-10, ceteth-15, ceteth-20, ceteth-25, ceteth-50, ceteth-100, ceteareth-10, ceteareth-15, ceteareth-20, ceteareth-25, steareth-2, steareth-10, steareth-20, steareth-25, steareth-100, laureth-10, trideceth-10, PEG-4-PPG-7 C13/15 alcohol, PPG-8-ceteth-5, PPG-4-laureth-5, and combinations thereof.

Another type of nonionic surfactant which may be used in compositions according to an example of the present specification is an alkoxylated fatty ester type of surfactant. Alkoxylated fatty esters may be esters of fatty acids with one or more alkoxy groups. In principle, any type or number of alkoxy groups may be used. For example, ethylene glycol or polyethylene glycol, propylene or polypropylene glycol, glyceryl or polyglyceryl, butylene or polybutylene glycol may be used. In a further example, combinations of the above may be used, such as a combination of glyceryl and polyethylene glycol.

Suitable non-limiting examples of alkoxylated fatty esters include glyceryl stearate, glyceryl cetate, PEG-2 laurate, PEG-4 laurate, PEG-10 laurate, PEG-20 laurate, PEG-2-PPG-5 laurate, PEG-2 stearate, PEG-20 stearate, PEG-100 stearate, PPG-2 isostearate, PPG-15 isostearate, PPG-15 stearate, and the like.

Another type of nonionic surfactant which may be used in compositions according to the present specification is an alkanolamide type of surfactant.

Suitable non-limiting examples of alkanolamides which may be used in compositions according to the present specification include coco monoethanolamide (MEA), coco diethanolamide (DEA), lauryl MEA, lauryl DEA, myristyl MEA, myristyl DEA, cetyl MEA, cetyl DEA, stearyl MEA, stearyl DEA, oleyl MEA, oleyl DEA, and combinations thereof.

Another type of nonionic surfactant which may be used in compositions according to the present specification is an alkyl glycoside type of surfactant. Alkyl glycosides may be condensation products of fatty alcohols with a number of sugars.

While each molecule of an alkyl glycoside contains an integer number of sugars, the ensemble average may be a noninteger number. For example, an alkyl glycoside surfactant could contain glucose as the sugar, and could be included as a mixture of compounds with 2, 3, 4 and 5 glucose units, such that the ensemble average contains 3.4 glucose units.

Suitable non-limiting examples of alkyl glycosides which may be used in compositions according to an example of the present specification include coco glucoside and lauryl glucoside.

Nonionic surfactants may be incorporated into compositions according to the present specification at concentrations ranging from 0% to 50% by weight. For example, a composition according to the present specification may contain at least one nonionic surfactant at a concentration ranging from 0.01% to 15% by weight. In another example, a composition according to the present specification may contain a nonionic surfactant at a concentration ranging from 0.1% to 10% by weight. In a further example, a composition according to the present specification may contain a nonionic surfactant at a concentration ranging from 0.1% to 5% by weight. All of the above concentrations are provided as weight percentages, relative to the total weight of the composition.

Compositions according to the present specification may also include cationic surfactants. Cationic surfactants may be any surfactant that contains a positive charge and does not contain a negative charge, such as, for example, quaternary ammonium salt surfactants and tertiary ammonia surfactants (which may form a quaternary ammonium surfactant in compositions with a pH of less than about 9). Additional types of cationic surfactants which may be used in compositions according to the present specification include esterquat and amidoamine surfactants.

Suitable non-limiting examples of cationic surfactants which may be used in compositions according to the present specification include cetrimonium chloride, cetrimonium methosulfate, steartrimonium chloride, steartrimonium methosulfate, behentrimonium chloride, behentrimonium methosulfate, arachidtrimonium chloride, arachidtrimonium methosulfate, stearamidopropyl trimonium chloride, behenamidopropyl trimonium methosulfate, N,N-dimethylstearylamine, N,N-dimethylcetylamine, and the like.

Cationic surfactants may be incorporated in compositions according to the present specification in concentrations ranging from 0% to 50% by weight, for example from 0.01% to 15% by weight. In another example, cationic surfactants may be included at concentrations ranging from 0.1% to 10% by weight. In a further example, cationic surfactants may be included in compositions according to the present specification at concentrations ranging from 1% to 5% by weight. A still further example may contain cationic surfactants in a composition according to the present specification in the range of 0.1% to 2% by weight, with all weights being relative to the total weight of the composition.

Compositions according to examples the present specification may also include amphoteric surfactants, which may be surfactants which have a hydrophilic part which has both acidic and basic hydrophilic groups and which behaves in an acidic or basic manner, depending on the conditions. Unlike zwitterionic surfactants, amphoteric surfactants do not permanently bear a charge. Amphoteric surfactants may include surfactants based on aliphatic amines having carboxy, sulfo or phosphono side chains. Amphoteric surfactants include such surfactants as N-alkyl glycines, N-alkyl propionic acids, N-alkyl aminobutyric acids, N-alkyl taurines, N-alkyl sarcosines, and amine oxide surfactants.

Suitable non-limiting examples of amphoteric surfactants which may be included in compositions according to the present invention include lauryldimethylamine oxide, disodium capryloamphodiacetate, disodium cocoamphodiacetate, disodium lauroamphodiacetate, disodium cocoamphodipropionate, and combinations thereof.

Amphoteric surfactants may be included in compositions according to the present specification at concentrations ranging from 0% to 50% by weight. For example, a composition according to the present specification may contain an amphoteric surfactant at a concentration ranging from 0.01% to 25% by weight. In another example, a composition according to the present specification may contain an amphoteric surfactant at a concentration ranging from 0.1% to 15% by weight. In a further example, one or more amphoteric surfactants may be present in a composition according to the present specification at a concentration ranging from 1% to 10% by weight. In a still further example, an amphoteric surfactant may be present in a composition according to the present specification at a concentration ranging from 0.1% to 5% by weight, with all weights being relative to the total weight of the composition.

Compositions according to the present specification may also include zwitterionic surfactants. Zwitterionic surfactants may be surfactants which bear both a positive charge and a negative charge. Some types of zwitterionic surfactants are capable of forming intramolecular salts. Zwitterionic surfactants include the betaine type of surfactants as well as the sultaine type of surfactants.

Suitable non-limiting examples of zwitterionic surfactants which may be included in compositions according to the present specification include cocamidopropyl betaine, cocamidopropyl sultaine, cocamidopropyl hydroxysultaine, laurylamidopropyl betaine, laurylamidopropyl sultaine, stearylamidopropyl betaine, oleyl betaine, myristyl betaine, stearyl betaine, cetyl betaine, and the like. Combinations of the above are also suitable for incorporation into compositions according to the present specification.

Zwitterionic surfactants may be included in compositions according to an example of the present specification at concentrations ranging from 0% to 50% by weight. For example, a composition according to the present specification may contain a zwitterionic surfactant at a concentration ranging from 0.01% to 25% by weight. In another example, a composition according to the present specification may contain a zwitterionic surfactant at a concentration ranging from 0.1% to 15% by weight. In a further example, one or more zwitterionic surfactants may be present in a composition according to the present specification at a concentration ranging from 1% to 10% by weight. In a still further example, a zwitterionic surfactant may be present in a composition according to the present specification at a concentration ranging from 0.1% to 5% by weight, with all weights being relative to the total weight of the composition.

Compositions according to the present specification may additionally include at least one analgesic compound. An analgesic compound may be any compound which provides relief from pain. Analgesic compounds include, but are not limited to, anesthetic compounds which produce relief from pain by removing sensation. Non-steroidal anti-inflammatory drugs (NSAIDs) may also be considered analgesic compounds, and may include COX-2 inhibitors, as well as other NSAIDs. Opioids may be another type of analgesic compound.

Analgesic compounds may be topically applied. In other words, topical analgesics may be compounds which produce analgesia when applied topically to the skin. Topical analgesics diffuse through the skin to the site of action, and may act on the nerves that sense muscle pain, joint pain, or a number of other types of pain. Topical analgesic compounds may also include compounds which cannot diffuse across the skin, but may act as local analgesics. A particular analgesic compound may be topical due to the composition which is used to administer the analgesic compound. For example, diclofenac may be administered orally to produce systemic analgesia, but may also be formulated into a cream as a topical analgesic.

Compositions according to the present specification may include at least one topical analgesic compound. Non-limiting examples of topical analgesic compounds may include bendazac, benzyldamine, bufexamac, diethylamine salicylate, etofenamate, felbinac, fepradinol, feprazone, flufenamic acid, ibuprofen, imidazole salicylate, isonixin, ketoprofen, nimesulide, phenylbutazone, piketoprofen, piroxicam, proglumetacin, sadicylamide, salol, salicylic acid, suxibuzone, ufenamate, and combinations and/or salts thereof.

Additional non-limiting examples of topical analgesic compounds which may be used in accordance with the present specification include *Aleurites moluccanus bakoly* seed oil, *Aloe barbadensis* leaf extract, aluminum acetate, benzyl alcohol, camphor, capsaicin, *Capsicum frutescens* fruit, *Capsicum frutescens* resin, *Cedrus deodora* wood extract, decursinol, diphenylhydramine, benzocaine, *Ginkgo* leaf terpenoids, hydrocortisone, *Juniperus communis* sprout extract, *Juniperus oxycedrus* wood tar, lauryl PEG-8 dimethicone, lidocaine, *Meconopsis horridula* flower extract, menthol, methyl nicotinate, methyl salicylate, ethyl salicylate, *Ocimum tenuiflorum* oil, *Papaver rhoeas* seed extract, pentafluoropropane, phenol, *Pinus palustris* resin extract, *Piper longum* fruit, *Piper nigrum* fruit, *Piper nigrum* seed, pramocaine, *Saposhnikovia divaricata* root extract, humic acid, turpentine, and combinations and/or salts thereof.

The at least one analgesic compound may be included in compositions according to the present specification at concentrations ranging from 0.01% to 30% by weight. For example from 0.1 to 25% by weight. In another example, a composition according to the present specification may contain at least one analgesic compound at a concentration ranging from 0.5 to 10% by weight, relative to the total weight of the composition. A still further example may contain at least one analgesic compound at a concentration within the range of from 0.1% to 5% by weight, relative to the total weight of the composition.

Compositions according to the present specification may also include a number of additive ingredients. Such additive ingredients may include a natural polymer, a synthetic polymer, a semi-synthetic polymer, an antibacterial agent, a fragrance, a humectant, a dye, a pigment, an exfoliant, a conditioning agent, a plant extract, plant matter, an essential oil, an oil, a wax, a silicone, a silicone wax, a chelator, a vitamin, an alkali metal halide, and combinations thereof. The inclusion of a component which is already listed above as an additive may refer to the inclusion of an additional compound within the provided class. A brief, non-limiting description of each type of additive follows.

Natural polymers may be polymers which are assembled enzymatically as a natural result of biological processes. Natural polymers may be added to an example of compositions according to the present specification as thickeners, natural conditioners, emulsion stabilizers, or to confer other such properties to the composition. Such natural polymers may be extracted from natural sources. Non-limiting examples of natural polymers include sugar-based polymers (for example, cellulose), polymers of modified sugar units such as nucleic acid chains, proteinaceous polymers (for example, silk, keratin, and collagen), and combinations thereof. Natural polymers may be in a variety of lengths, and may remain natural polymers according to the present specification if the length of the polymer is adjusted chemically after extraction of the polymer. For example, hydrolyzed keratin may be a natural polymer according to the present specification, although the hydrolysis of the keratin may be carried out following extraction of the keratin from natural sources. Examples of natural polymers include honey, cellulose and xanthan gum.

Synthetic polymers may be polymers which are assembled from monomeric units by synthetic processes. Synthetic polymers may be added an example of compositions according to the present specification as thickeners, conditioners, deposition aids, emulsion stabilizers, or to confer other such properties to a composition according to the present specification. Non-limiting examples of synthetic polymers which may be used in compositions according to the present specification include carbomer, acrylates/acrylamide copolymers, acrylamidopropyltrimonium chloride/acrylates copolymers, polyethylene glycol polymers, polypropylene glycol polymers, polyquaternium-1, polyquaternium-2, polyquaternium-5, polyquaternium-7, polyquaternium-11, polyquaternium-15, polyquaternium-22, polyquaternium-28, and combinations thereof.

Semi-synthetic polymers may be polymers which involve both natural components and synthetic components. Semi-synthetic polymers may be added to an example of compositions according to the present specification as thickeners, conditioners, emulsion stabilizers, deposition aids, or to provide other such properties to a composition according to the present specification. Semi-synthetic polymers may be chemically modified natural polymers; semi-synthetic polymers may also be synthetically assembled polymers of natural monomer units. Non-limiting examples of semi-synthetic polymers which may be used in compositions according to the present specification include hydroxyethyl cellulose, quaternized hydroxyethyl cellulose (which may be called polyquaternium-10), quaternized protein hydrolysates, crosslinked protein hydrolysates, and combinations thereof.

Compositions according to the present specification may also include at least one antibacterial agent. An antibacterial agent may be any agent which assists in the removal of bacteria, kills bacteria, or arrests bacterial growth. Any given antibacterial agent may belong to one or more than one of the aforementioned classes.

Suitable non-limiting examples of antibacterial agents include antiseptics, triclosan, benzethonium salts, benzalkonium salts, compounds which inhibit the 70S (bacterial) ribosome, compounds which reduce the integrity of the bacterial cell wall, and compounds which sequester nutrients—for example, metal ions—that bacteria require. Additional non-limiting examples of antibacterial agents include ethanol, isopropanol, aminoglycosides (such as neomycin), cephalosporins (such as cefalexin), lincosamides (such as lincomycin), tetracyclines (such as doxycycline), penicillins (such as amoxicillin), chelating agents (such as ethylenediaminetetraacetic acid), and combinations thereof.

Fragrances may be components or compositions which may produce an olfactory sensation in an individual. Fragrances may contain a single component; fragrances may also be mixtures of multiple separate components. Non-limiting examples of fragrance components which may be used in compositions according to the present specification include aldehydes, ketones, aromatic hydrocarbons, aromatic alcohols and combinations thereof. Examples of fragrance ingredients may include alpha-hexyl cinnamal, vanillin, citral, eugenol, geraniol, limonene, and citronellol.

Humectants may be hygroscopic substances, or substances which attract water. Humectants may be added to an example of compositions according to the present specification in order to maintain moisture on the skin to which the analgesic cleansing composition is applied. Non-limiting examples of humectants which may be used in compositions according to the present specification may include polyols, urea, honey, aloe vera gels, glycerol, sorbitol, glycols, propylene glycol, and butylene glycol.

Dyes and pigments may be compounds which confer color to a composition or a surface to which a composition of the present specification is applied. Dyes and pigments may be added to an example of compositions according to the present specification in order to imbue the composition with a consumer-acceptable color. Non-limiting examples of dyes and pigments which may be used in compositions according to the present specification include titanium dioxide, mica, violet 2, red 4, red 6, red 7, red 33, red 40, blue 1, blue 4, yellow 5, yellow 6, yellow 10, orange 4, orange 5, orange 10, and combinations thereof.

Exfoliants may be particles which are non-dissolvable solids which may be dispersed throughout an example of compositions according to the present specification in order to act as an abrasive when the composition is used to cleanse the skin. The abrasive properties of the exfoliating particles may act to remove dead skin cells from the surface of the skin in order to allow deeper action of the at least one surfactant, promote regeneration of the skin, and provide more *facile* diffusion of the at least one analgesic compound across the skin to the site of action. Suitable non-limiting examples of exfoliants which may be used in compositions according to the present specification include *actinidia chinensis* (kiwi) seed, alumina, aluminum iron silicates, aluminum silicate, amethyst powder, amorphophallus konjac root powder, *arachis hypogaea* (peanut) flour, attapulgite, *avena sativa* (oat) bran, *avena sativa* (oat) kernel flour, *avena sativa* (oat) kernel meal, *bambusa arundinacea* stem powder, calcium carbonate, calcium phosphate, calcium pyrophosphate, calcium sulfate, *carya illinoensis* (pecan) shell powder, chalk, chitin, *citrus tangerina* (tangerine) peel, *cocos nucifera* (coconut) shell powder, colloidal oatmeal, conchiolin powder, coral powder, *corylus avellana* (hazel) shell powder, diamond powder, diatomaceous earth, dicalcium phosphate, dicalcium phosphate dihydrate, dolomite, egg shell powder, eijitsu, elguea clay, emerald, *fragaria vesca* (strawberry) seed, fuller's earth, *glycine soja* (soybean) flour, *helianthus annuus* (sunflower) seed meal, *hordeum distichon* (barley) seed flour, *hordeum vulgare* powder, *hordeum vulgare* seed flour, hydrated silica, hydroxyapatite, illite, *juglans mandshurica* (walnut) shell powder, *juglans regia* (walnut) shell powder, kaolin, kurumi kaku, lauryl acrylate/VA crosspolymer, lithothamnium calcarum powder, lithoammium corallioides powder, loess, luffa *cylindrica* fruit, magnesium potassium fluorosilicate, magnesium sodium fluorosilicate, magnesium trisilicate, *melaleuca* alternifolia leaf powder, microcrystalline cellulose, montmorillonite, moroccan lava clay, mother of pearl, myristyl betaine, *oenothera biennis* (evening primrose) seed, *olea europaea* (olive) fruit, *olea europaea* (olive) husk powder, *olea europaea* (olive) seed powder, *oryza sativa* (rice) bran, *oryza sativa* (rice) germ powder, oubaku, oyster shell powder, *papaver somniferum* seed, perlite, *persea gratissima* (avocado) fruit powder, *phaseolus radiatus* seed starch, platinum powder, polyethylene, potassium undecylenoyl glutamate, *prunus amygdalus dulcis* (sweet almond) seed meal, *prunus amygdalus dulcis* (sweet almond) shell powder, *prunus armeniaca* (apricot) seed powder, *prunus mume* fruit, *prunus persica* (peach) seed powder, pumice, quartz, *rubus idaeus* (raspberry) seed, salt mine mud, sand, sea salt, *secale cereale* (rye) seed flour, silica, sodium bicarbonate, sodium hydroxypropyl starch phosphate, sodium magnesium fluorosilicate, sodium silicoaluminate, *symphytum officinale* leaf powder, talc, *theobroma cacao* (cocoa)

shell powder, tin oxide, titanium oxynitride, topaz, touki, tricalcium phosphate, *triticum vulgare* (wheat) bran, *triticum vulgare* (wheat) germ powder, *triticum vulgare* (wheat) kernel flour, *triticum vulgare* (wheat) starch, *vaccinium angustifolium* (blueberry) seed, *vaccinium macrocarpon* (cranberry) seed, volcanic ash, wood powder, yokuinin, *zea mays* (corn) cob meal, *zea mays* (corn) cob powder, *zea mays* (corn) kernel meal, *zea mays* (corn) seed flour, *zea mays* (corn) starch, zirconium silicate, or combinations thereof.

Conditioning agents may be components which act to preserve existing moisture by creating a hydrophobic barrier between the moisturized skin and the air, and may be incorporated into an example of compositions according to the present specification for this purpose. Non-limiting examples of conditioning agents include the polyquaternium class of polymers, fatty alcohols and polyols.

Plant extracts may be natural compounds or mixtures of compounds produced in a plant which contain a number of agents that have either a real or perceived benefit to the skin, or to the composition as a whole. The inclusion of some plant extracts may improve consumer acceptance of a cleansing composition on the basis of these benefits, or a consumer preference for naturally produced compositions over synthetically produced compositions. Plant extracts may include oils, fragrance ingredients, fatty acids, and/or various other components depending on the extraction methods employed and any subsequent processing that is performed. Non-limiting plant extracts which may be used in compositions according to the present specification may include *Ocimum basilicum* extract, *Calendula officinalis* extract, *Matricaria chamomilla* extract, *Oenothera biennis* extract, *Zingiber officinale* extract, *Jasminum* extracts, *Lavandula angustifolia* extract, *Mentha x piperita* extract, *Rosmarinus officinalis* extract, Rosa extracts, *Hypericum perforatum* extract, *Syringa vulgaris* extract, and combinations thereof.

Plant matter may be plant material which may be incorporated into an example of compositions according to the present specification. Such plant material may provide abrasive properties as exfoliants, fragrance properties, or as a thickener. The incorporation of plant material into cleansing compositions may improve consumer acceptance, which may be based on the perception of the natural qualities of the compositions including plant matter. Non-limiting examples of plant matter which may be incorporated in compositions according to the present specification include whole flowers, flower petals, stems, seeds, roots, and fruits. Non-limiting examples of plant sources which may provide the plant matter include Citrus plants, *Malus domestica* plants, *Hypericum perforatum* plants, and *Zingiber officinale* plants.

Essential oils may be a particular type of plant extract, which may include volatile aroma compounds from the plant from which the essential oil is extracted. The extraction methods used may determine the composition of the essential oil. Possible extraction methods may include steam distillation, pressure, solvent extraction with organic solvents, solvent extraction with carbon dioxide, and oil extractions, for example. In principle, any type of plant may be used to prepare an essential oil, such as *Ocimum basilicum* essential oil, *Calendula officinalis* essential oil, *Matricaria chamomilla* essential oil, *Oenothera biennis* essential oil, *Zingiber officinale* essential oil, *Jasminum* essential oils, *Lavandula angustifolia* essential oil, *Mentha x piperita* essential oil, *Rosmarinus officinalis* essential oil, Rosa essential oils, *Hypericum perforatum* essential oil, and *Syringa vulgaris* essential oil.

Oils may be neutral, nonpolar substances that are viscous liquids at standard ambient temperature and pressure (1 atmosphere pressure, 25° Celsius). Oils may be included in an example of compositions according to the present specification in order to act as conditioning agents, or to replenish natural oils on the skin. Oils may include triglycerides, fatty alcohols, and mineral oils. Mineral oils may be oils that are prepared by distillation from crude oil. Non-limiting examples of oils which may be suitable for use in compositions according to the present specification include olive oil, vegetable oil, rapeseed oil, paraffinum liquidum, cetyl alcohol, stearyl alcohol, myristyl alcohol, octyldodecanol, oleyl alcohol, sunflower oil, corn oil, palm oil, soybean oil, sunflower oil, safflower oil, peanut oil, and combinations thereof.

Waxes may be compounds which have a large fatty content, and are solid at standard ambient temperature and pressure. Waxes may be malleable at standard ambient temperature and pressure. Waxes may have a melting point at or above about 45° Celsius (C). Waxes may be included in an example of compositions according to the present specification in order to improve rheological properties, act as conditioning agents, or to provide other such properties to the composition. Waxes include fatty esters, fatty ethers, hydrocarbons, primary alcohols, secondary alcohols, ketones and aldehydes. Waxes may be alkanes, alkenes, or alkynes, and may be aromatic, anti-aromatic or aliphatic. Waxes may be derived from plants, animals, or crude oil. Non-limiting examples of waxes which may be used in compositions according to the present specification include cetyl palmitate, lanolin, myricyl palmitate, Carnauba wax, candelilla wax, beeswax, montan wax, paraffin wax, and combinations thereof.

Silicone oils may be neutral compounds that are liquids at standard temperature and pressure. Silicone oils may be a type of oil, and may be included in an example of compositions according to the present specification for the same reasons noted above for oils. Silicone oils may be saturated with hydrocarbon components along a siloxy backbone, which may correspond to the Si—(O—Si)$_n$ chain. Silicone oils may also have functional groups incorporated therein. Such functional groups may include amines and alcohols. Non-limiting examples of silicone oils which may be incorporated in compositions according to the present specification include dimethicone, cyclomethicone, dimethiconol, PEG-12 dimethicone, PEG-8 dimethicone, amodimethicone, alkyl methicones, and combinations thereof.

Silicone waxes may be silicone compounds which are solid at standard ambient temperature and pressure. Silicone waxes may be a type of waxes, and may be included in an example of compositions according to the present specification for the same reasons noted above for waxes. Silicone oils may have a melting point at or above about 45° C. Non-limiting examples of silicone waxes which may be used in compositions according to the present specification include alkyl methicones, Silwax A-08, Silwax C, Silwax D-02, Silwax F, Silwax S, and combinations thereof.

Chelators may be compounds which coordinate metal ions. Chelators may be included in an example of compositions according to the present specification as antibacterial agents, preservatives, pH regulators, or to provide other such properties to the composition. Non-limiting examples of chelators which may be used in compositions according to the present specification include natural polyacids (such as citric acid), phosphate salts (such as disodium pyrophosphate), bisphosphonates (such as etridronic acid), aminocarboxylic acids (such as ethylenediaminetetraacetic acid (EDTA), diethylenetriaminepentaacetic acid (DPTA), ethylenediamine-N,N'-disuccinic acid (EDDS), ethylenediamine-N,N'-diglutaric acid (EDDG), glycinamide-N,N'-disuccinic acid (GADS), and ethylenediamine-N,N'-bis(ortho-hydroxyphenyl acetic acid) (EDDHA)), and combinations and/or salts thereof.

Vitamins may be organic compounds which an organism may require in limited quantities, and which the organism that may require the vitamin cannot synthesize from other precursors. Vitamins, or vitamin derivatives, may be included in an example of compositions according to the present specification as conditioning agents, preservatives, antioxidants, or to improve consumer acceptance of the composition. Non-limiting examples of vitamins which may be used in compositions according to the present specification include vitamin A (retinol), vitamin $B_6$ (pyroxidine), vitamin $B_7$ (biotin), vitamin $B_{12}$ (cyanocobalamin), vitamin C (ascorbic acid), vitamin E (tocopherols), and vitamin K (phylloquinone). For the purposes of the present specification, "vitamin" also includes derivatives and stereoisomers of vitamins, such as polyoxypropylene (2) polyoxyethylene (5) tocopherol ether, and isoascorbic acid.

Alkali metal halides may be salts of alkali metals and halogen atoms. Alkali metal halides may be included in an example of compositions according to the present specification as thickeners, ionic strength modulators, or to confer other such properties to the composition. Alkali metal halides may be neutral compounds. Non-limiting examples of alkali metal halides which may be used in compositions according to the present specification include lithium fluoride, lithium chloride, lithium bromide, lithium iodide, sodium fluoride, sodium chloride, sodium bromide, sodium iodide, potassium fluoride, potassium chloride, potassium bromide, potassium iodide, and combinations thereof.

Additives may be incorporated into compositions according to the present specification at concentrations ranging from 0% to 30% by weight. For example, from 0.01% to 20% by weight. In another example, additives may be incorporated into compositions according to the present specification at concentrations ranging from 0.1% to 10% by weight. The percentages by weight are relative in each case to the total weight of the composition.

Compositions according to the present specification may also include a deposition aid. A deposition aid may be a compound or macromolecular structure that assists in the deposition of the analgesic compound on the skin. Because the skin may be negatively charged, the deposition aid may be positively charged. In another example, the deposition aid is uncharged. In still another example, the deposition aid is zwitterionic, having both positive and negative charges. Deposition aids may come in a variety of forms, including cationic polymers and encapsulants. Non-limiting examples of cationic polymer deposition aids which may be used in compositions according to the present specification include polyquaternium-7, polyquaternium-10, polyquaternium-11, and the like. Encapsulants may be another type of deposition aid, and may encapsulate at least one analgesic compound by providing a shell. The size of the encapsulant may be determined in order to provide enhanced deposition on the skin. For example, the encapsulant may be 10 nanometers (nm) in diameter. In another example, the encapsulant may be 20 nm in diameter. In another example, the encapsulant may be 100 nm in diameter. In still another example, the encapsulant may be from 150 to 200 nm in diameter.

Deposition aids may also assist the deposition of the analgesic compound onto the skin by a reversible tethering mechanism. For example, a deposition aid may be attached to the analgesic compound by an ester bond, which may be chosen so as to be readily hydrolyzed in an alkaline environment. The deposition aid may be attracted to the skin by charge-charge interactions, where the analgesic compound may be hydrolyzed from the encapsulation aid by an esterase or hydroxide ion. Such a deposition aid may provide a high local concentration of the analgesic compound on the surface of the skin, and as a result may increase the quantity of analgesic compound which is able to diffuse through the skin to the site of action.

Deposition aids may be used in compositions according to the present specification at concentrations ranging from 0.001% to 30% by weight. For example, a deposition aid may be present in a composition according to the present specification at a concentration ranging from 0.01% to 20% by weight. In another example, a deposition aid may be present in a composition according to the present specification at a concentration ranging from 0.1% to 10% by weight. In a still further example, a deposition aid may be incorporated in a composition according to the present specification at a concentration range of from 0.5% to 5% by weight. In each case, the weight percent is relative to the total weight of the composition.

The wash-off analgesic cleansing composition according to the present specification may be provided in the form of a solid or a liquid. A solid wash-off analgesic cleansing composition according to the present specification may take the form of a bar soap. A liquid wash-off cleansing composition according to the present specification may take the form of a liquid hand soap, liquid body soap, liquid shampoo composition or a liquid conditioner composition. For the purposes of the present specification, "liquid" may be used generally to refer to a fluid, and is meant to include both creams and gels, as well as foamable liquids.

Turning now to the figures, FIG. 1 is a diagram of an exemplary container (100) dispensing an analgesic cleansing composition (104) according to an example of the principles described herein. The container (100) may be equipped with an opening (102) capable of dispensing the analgesic cleansing composition (104). The opening (102) may dispense the analgesic cleansing composition (104) by a plunger type mechanism (106), or another appropriate dispenser. The opening (102) may dispense the analgesic cleansing composition (104) onto an area of the skin. For example, the opening (102) may dispense the analgesic cleansing composition (104) onto a hand (108) of a user. The container (100) shown in FIG. 1 is exemplary and does not represent all types of dispensers or shapes of containers which may be used to dispense the analgesic cleansing composition (104). Another type of dispensing container (100) may include a simple opening allowing for the dispensing of the analgesic cleansing composition (104), which container (100) may have a cap.

The liquid analgesic cleansing composition (104) according to the present specification may be either a wash-off analgesic cleansing composition according to the principles described herein, or may be a leave-on analgesic cleansing composition, according to the principles described herein. The liquid analgesic cleansing composition (104) according to the present specification may also include a cosmetically suitable carrier.

Cosmetically suitable carriers may be any liquid that is suitable for cosmetic use which may be able to dissolve or disperse the at least one surfactant, the at least one analgesic compound, and any optional additives that may be included in the liquid analgesic cleansing composition (104) according to the present specification. Non-limiting examples of cosmetically suitable carriers which may be suitable for use in compositions according to the present specification include aqueous carriers, alcoholic carriers, and aqueous-alcoholic carriers. For example, the cosmetically suitable carrier could be water. In another example, the cosmetically suitable carrier could be ethanol. In yet another example, the cosmetically suitable carrier could be isopropanol. In another example, the cosmetically suitable carrier could be a mixture of water and ethanol. In a further example, the cosmetically suitable carrier could include glycerin.

Previous preparations of liquid cleansing compositions have not included analgesic compounds for a number of reasons, which may include that the desire of an individual to simultaneously cleanse their skin and relieve muscle pain had not been previously identified, as well as possible formulation difficulties associated with incorporating analgesic compounds into liquid cleansing compositions while also retaining the efficacy of the analgesic compounds.

The present specification is also directed to a leave-on analgesic cleansing composition. Such a leave-on analgesic cleansing composition may include a cosmetically suitable carrier, at least one surfactant, and at least one analgesic compound.

A leave-on analgesic cleansing composition according to the present specification may contain a cosmetically suitable carrier, as defined above, in concentrations ranging from 40% to 99% by weight. For example, a leave-on analgesic cleansing composition according to the present specification may contain a concentration of a cosmetically suitable carrier in the range of 50% to 90% by weight. In another example, the concentration of the cosmetically suitable carrier in a leave-on analgesic cleansing composition according to the present specification may be in the range of 60% to 85% by weight. A still further example may provide a concentration of the cosmetically suitable carrier in a leave-on analgesic cleansing composition according to the present specification in the range of 65% to 75% by weight. In each case, the percent of the composition by weight that is provided by the cosmetically suitable carrier is relative to the weight of the total composition.

A leave-on analgesic cleansing composition according to the present specification may contain at least one surfactant, as defined above, in concentrations ranging from 0.1% to 50% by weight. For example, a leave-on analgesic cleansing composition according to the present specification may contain a concentration of between 1% and 30% by weight of at least one surfactant. In another example, a leave-on analgesic cleansing composition according to the present specification may contain a concentration of between 4% and 20% by weight of at least one surfactant. In a still further example, a leave-on analgesic cleansing composition according to the present specification may contain a concentration of between 5% and 15% by weight of at least one surfactant. In each case, the percent of the composition by weight that is provided by the at least one surfactant is relative to the weight of the total composition.

A leave-on analgesic cleansing composition according to the present specification may contain at least one of analgesic compound, as defined above, in concentrations ranging from 0.01% to 30% by weight. For example, a leave-on analgesic cleansing composition according to the present specification may contain a concentration of between 0.1% and 25% by weight of at least one analgesic compound. In another example, a leave-on analgesic cleansing composition according to the present specification may contain a concentration of between 0.5% and 10% by weight of at least one analgesic compound. In yet another example, a leave-on analgesic cleansing composition according to the present specification may contain a concentration of between 0.1% and 5% by weight of at least one analgesic compound.

A leave-on analgesic cleansing composition according to the present specification may also contain a number of additives, which may be chosen from a natural polymer, a synthetic polymer, a semi-synthetic polymer, an antibacterial agent, a fragrance, a humectant, a dye, a pigment, an exfoliant, a conditioning agent, a plant extract, plant matter, an essential oil, an oil, a silicone oil, a wax, a silicone wax, a chelator, a vitamin, an alkali metal halide, and combinations thereof, each of which may be as described above.

If the leave-on analgesic cleansing composition contains at least one antibacterial agent as an optional additive, the concentration of the at least one antibacterial agent in a leave-on analgesic cleansing composition according to the present specification may depend on the choice of the antibacterial agent. For example, if the at least one antibacterial agent is chosen to not include ethanol or isopropanol, then the concentration of the at least one antibacterial agent in a leave-on analgesic cleansing composition according to the present specification may be in the range of 0.0001% to 10% by weight, such as, for example a concentration ranging from 0.001% to 8% by weight. In another example, a leave-on analgesic cleansing composition according to the present specification may contain a concentration of from 0.01% to 5% by weight of at least one antibacterial agent. A still further example may contain a concentration of at least one antibacterial agent other than ethanol and isopropanol in a leave-on analgesic cleansing composition according to the present specification in the range of 0.1% to 1% by weight. In each case, the concentration by weight is relative to the total weight of the composition.

If the leave-on analgesic cleansing composition includes ethanol or isopropanol as at least one antibacterial agent, a concentration of at least 50% by weight may be used. For example, a leave-on analgesic cleansing composition according to the present specification which contains ethanol or isopropanol as one of the at least one antibacterial agent may contain a concentration of at least 60% by weight of the at least one antibacterial agent. Another example may contain ethanol or isopropanol as one of the at least one antibacterial agent at a concentration of at least 70% by weight, such as, for example, a concentration of at least 75% by weight. In each case, the concentration by weight is relative to the total weight of the composition.

Additionally, if the leave-on analgesic cleansing composition includes ethanol or isopropanol as at least one of the optional at least one antibacterial agent, then the ethanol or isopropanol may also optionally provide the cosmetically suitable carrier.

Figure 2:
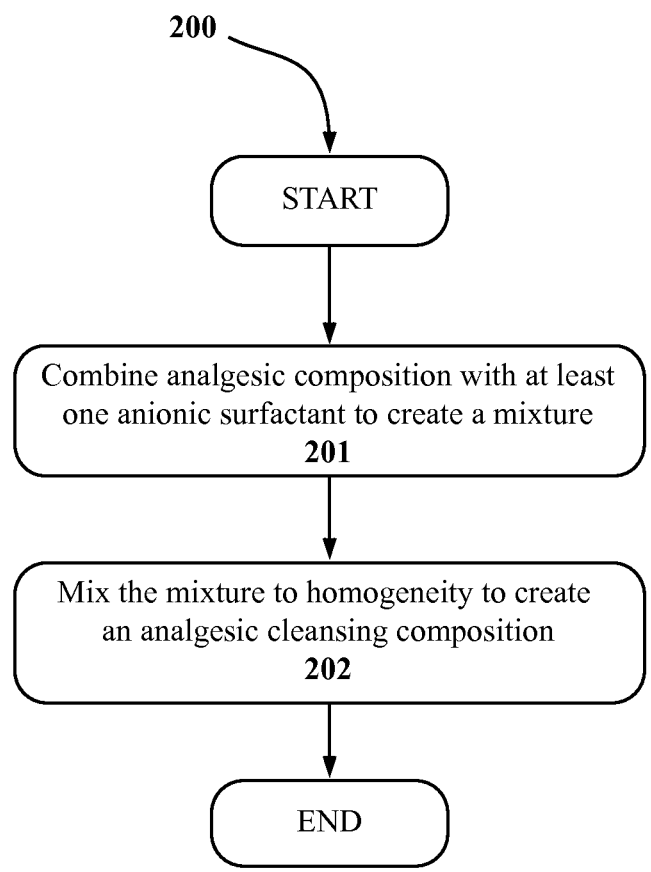
FIG. 2 is a flowchart of a method for making an analgesic cleansing composition according to an example of the principles described herein.

The present specification is also directed to a method of making an analgesic cleansing composition. FIG. 2 provides a flowchart of a method (200) of making an analgesic cleansing composition according to an example of the principles described herein. Such an analgesic cleansing composition may be a leave-on analgesic cleansing composition.

The method (200) involves the combination (201) of at least one anionic surfactant with an analgesic composition to create a mixture. The at least one anionic surfactant may be prepared separately prior to admixture with the analgesic cleansing composition. The at least one anionic surfactant may be in the form of a solid or a liquid prior to admixture with the analgesic composition.

The analgesic composition may be a cleansing composition which contains at least one analgesic compound. Such an analgesic composition may contain at least one topical analgesic compound, as defined above. For example, an analgesic composition may include methyl salicylate as the at least one analgesic compound according to the methods described herein. The analgesic composition may be either solid or a liquid prior to admixture with the at least one anionic surfactant.

The analgesic composition may include additional components, such as a cosmetically suitable carrier, an antibacterial agent, a deposition aid, a natural polymer, a synthetic polymer, a semi-synthetic polymer, a fragrance, a humectant, a dye, a pigment, an exfoliant, a conditioning agent, a plant extract, plant matter, an essential oil, an oil, a wax, a silicone oil, a silicone wax, a chelator, a vitamin, an alkali metal halide, and combinations thereof. Such additional components may also be incorporated into the analgesic cleansing composition (which may be an analgesic soap composition) separately from the analgesic composition, or may be omitted entirely.

If the analgesic cleansing composition also includes an encapsulating deposition aid, the preparation of the analgesic composition may also include an encapsulation operation. Such an encapsulation operation may be accomplished by a number of chemical reactions which, when taken together, serve to assemble a capsule or an ensemble of capsules around the at least one analgesic compound. In some examples, the encapsulation operation encapsulates a fraction of the at least one analgesic compounds, leaving some portion of the at least one analgesic compound not encapsulated. For example, the encapsulation operation may encapsulate from 10% to 100% by weight of the at least one analgesic compound, relative to the total weight of the at least one analgesic compound. In another example, the encapsulation operation may encapsulate from 20% to 90% by weight of the at least one analgesic compound, relative to the total weight of the at least one analgesic compound. In a still further example, the encapsulation operation may encapsulate from 30% to 60% by weight of the at least one analgesic compound, relative to the total weight of the at least one analgesic compound.

Following the encapsulation operation, the analgesic composition may be prepared by mixture of at least one analgesic compound, which may optionally be encapsulated, with any other additives which may be part of the analgesic composition.

The analgesic cleansing composition is then mixed (201) with the at least one anionic surfactant composition to prepare a mixture. The mixture may be prepared either before or after the separate addition of any additives.

Additionally, the method may also include a mixing operation (202). Such a mixing operation may make homogenous the mixture of the at least one anionic surfactant and the analgesic composition to generate the analgesic cleansing composition, which may be a leave-on cleansing composition, such as the liquid form (104) of an example of a composition according to the present specification. The mixing operation may be performed either before or after the separate addition of any additives.

The method may also include additional operations not diagramed in FIG. 2, such as the extrusion of the homogenous mixture from a plodder, cutting of the extruded mixture into slugs, and pressing the slugs in a soap press, and other operations such as the application of heat to assist mixing to homogeneity. Other methods may also be used to produce a composition according to the invention.

The analgesic cleansing composition produced by the above method (200), which may be an analgesic cleansing composition, may contain a sufficient amount of a topical analgesic compound to provide analgesia after contact with skin. Such a sufficient amount may be dependent on the choice of the at least one analgesic compound, and may be determined experimentally.

In one example, a sufficient amount of the at least one analgesic compound may be achieved by including the at least one analgesic compound in an analgesic cleansing composition at a concentration of from 0.01% to 30% by weight. In another example, a sufficient amount of the at least one analgesic compound may be achieved by including the at least one analgesic compound in an analgesic cleansing composition at a concentration of from 0.1% to 25% by weight. In a still further example, a sufficient amount of the at least one analgesic compound may be achieved by including the at least one analgesic compound in an analgesic cleansing composition at a concentration of from 0.5% to 5% by weight. In each case, the concentrations by weight are relative to the total weight of the composition.

Figure 3:
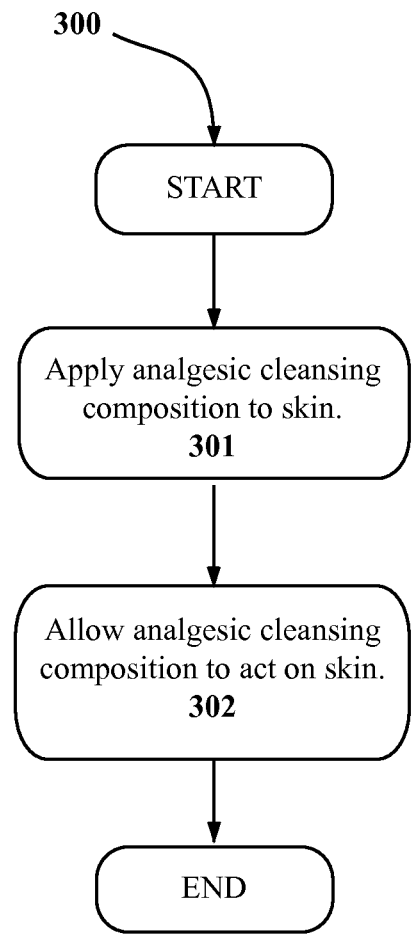
FIG. 3 is a flowchart of a method for using an analgesic cleansing composition according to an example of the principles described herein.

The present specification is also directed to a method (300) of using an analgesic cleansing composition to relieve muscle pain. FIG. 3 provides a flowchart of a method (300) for using an analgesic cleansing composition (104) according to an example of the principles described herein. Such an analgesic cleansing composition may be a wash-off or a leave-on analgesic cleansing composition.

The method (300) of using the analgesic cleansing composition according to the present specification may include applying (301) the analgesic cleansing composition to the skin. Such an analgesic cleansing composition may be a wash-off or a leave-on cleansing composition, and may include, in a cosmetically suitable carrier, at least one surfactant and at least one analgesic compound. The at least one analgesic compound may be encapsulated or unencapsulated. The analgesic cleansing composition may include additional additive ingredients selected from an antibacterial agent, a deposition aid, a natural polymer, a synthetic polymer, a semi-synthetic polymer, a fragrance, a humectant, a dye, a pigment, an exfoliant, a conditioning agent, a plant extract, plant matter, an essential oil, an oil, a wax, a silicone oil, a silicone wax, a chelator, a vitamin, an alkali metal halide, and combinations thereof.

If the analgesic cleansing composition being used is a leave-on analgesic cleansing composition, then the analgesic cleansing composition may be allowed (302) to act on the skin for a duration of from 5 seconds to 10 minutes, for example from 10 seconds to 5 minutes, or from 30 seconds to 2 minutes. For a leave-on cleansing composition, the action of the cleansing composition on the skin may be considered to end when the cosmetically suitable carrier has evaporated, although the analgesia may persist beyond the evaporation of the cosmetically suitable carrier.

If the analgesic cleansing composition being used is a wash-off analgesic cleansing composition, then the analgesic cleansing composition may be allowed (302) to act on the skin for a duration of from 5 seconds to 10 minutes, for example from 10 seconds to 5 minutes, or from 30 seconds to 2 minutes. After the analgesic composition is allowed to act on the skin, the analgesic cleansing composition is rinsed from the skin with water.

EXAMPLES

The examples that follow indicate analgesic cleansing compositions that may be prepared in accordance with the present specification. Unless otherwise indicated, the stated quantities are percentages by weight.

Example 1

Analgesic Soap Bar Composition

TABLE (I)

| Formulation Example 1 | Wt. % |
|---|---|
| Sodium Soap(s) | 65-91 |
| Additional Surfactant(s) | 0-5 |
| Analgesic Compound(s) | 0.5-5 |
| Chelating Agent(s) | 0.01-1 |
| Alkali Metal Halide(s) | 0-2 |
| Humectant(s) | 1-5 |
| Glycerin | 3-20 |
| Perfume | 0-2 |
| Water | 5-20 |

Example 2

Analgesic Wash-off Liquid Cleansing Composition

TABLE (II)

| Formulation Example 2 | Wt. % |
|---|---|
| Methyl Salicylate | 0.5-10 |
| Anionic Surfactant(s) | 4-10 |
| Nonionic Surfactant(s) | 0-5 |
| Zwitterionic Surfactant(s) | 0-10 |
| Polymeric Thickener | 0.5-5 |
| Preservative(s) | 0.2-2 |
| Exfoliant(s) | 0-5 |
| Water | q.s. 100 |

Example 3

Analgesic Leave-on Liquid Cleansing Composition (Aqueous)

TABLE (III)

| Formulation Example 3 | Wt. % |
|---|---|
| Anionic Surfactant(s) | 0.1-5 |
| Antibacterial Agent(s) | 0-5 |
| Deposition Aid(s) | 0.01-5 |
| Analgesic Compound(s) | 0.5-10 |
| Conditioning Agent(s) | 0-2 |
| Water | q.s. 100 |

Example 4

Analgesic Leave-on Liquid Cleansing Composition (Alcoholic)

TABLE (IV)

| Formulation Example 4 | Wt. % |
|---|---|
| Anionic Surfactant(s) | 0.1-5 |
| Deposition Aid(s) | 0-5 |

TABLE (IV)-continued

| Formulation Example 4 | Wt. % |
|---|---|
| Analgesic Compound(s) | 0.5-10 |
| Ethanol, 95% | q.s. 100 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An analgesic cleansing composition comprising: a cosmetically suitable carrier including at least 50 wt. % of one or more alcohols selected from the group consisting of isopropyl alcohol and ethanol based on the total weight of the analgesic cleansing composition;
and a leave-on cleansing composition, which comprises: at least one surfactant; and at least one analgesic compound to alleviate pain in a user, wherein the concentration of the at least one analgesic is from 0.01% to 30% by weight, relative to the total weight of the analgesic cleansing composition.

2. The analgesic cleansing composition of claim 1, in which the cosmetically suitable carrier comprises ethanol.

3. The analgesic cleansing composition of claim 1, in which the cosmetically suitable carrier comprises isopropanol.

4. The analgesic cleansing composition of claim 1, in which the cosmetically suitable carrier further comprises water.

5. The analgesic cleansing composition of claim 1, in which the at least one surfactant comprises an anionic surfactant.

6. The analgesic cleansing composition of claim 1, in which the at least one analgesic compound comprises a topical analgesic compound selected from *Aleurites moluccanus bakoly* seed oil, aluminum acetate, benzyl alcohol, camphor, capsaicin, *Capsicum frutescens* fruit, *Capsicum frutescens* resin, *Cedrus deodora* wood extract, decursinol, diphenylhydramine, benzocaine, *Ginkgo* leaf terpenoids, hydrocortisone, *Juniperus communis* sprout extract, *Juniperus oxycedrus* wood tar, lauryl PEG-8 dimethicone, lidocaine, *Meconopsis horridula* flower extract, menthol, methyl nicotinate, methyl salicylate, ethyl salicylate, *Ocimum tenuiflorum* oil, *Papaver rhoeas* seed extract, pentafluoropropane, phenol, *Pinus palustris* resin extract, *Piper longum* fruit, *Piper nigrum* fruit, *Piper nigrum* seed, pramocaine, *Saposhnikovia divaricata* root extract, humic acid, turpentine, bendazac, benzyldamine, bufexamac, diethylamine salicylate, etofenamate, felbinac, fepradinol, feprazone, flufenamic acid, ibuprofen, imidazole salicylate, isonixin, ketoprofen, nimesulide, phenylbutazone, piktoprofen, piroxicam, proglumetacin, sadicylamide, salol, salicylic acid, suxibuzone, ufenamate, or salts thereof.

7. The analgesic cleansing composition of claim 6, in which the at least one topical analgesic compound comprises methyl salicylate.

8. The analgesic cleansing composition of claim 1, further comprising at least one additive selected from a natural polymer, a synthetic polymer, a semi-synthetic polymer, an antibacterial agent, a fragrance, a humectant, a dye, a pigment, an exfoliant, a conditioning agent, a plant extract, plant matter, an essential oil, an oil, a wax, a silicone oil, a silicone wax, a chelator, a vitamin, a vitamin derivative, an alkali metal halide, and combinations thereof.

9. The analgesic cleansing composition of claim 8, in which at least one of the at least one additive increases the viscosity of the composition.

10. The analgesic cleansing composition of claim 1, further comprising a deposition aid.

11. The analgesic cleansing composition of claim 10, in which the deposition aid is cationally charged.

12. The analgesic cleansing composition of claim 10, in which the deposition aid encapsulates the at least one analgesic compound.

13. A method of producing an analgesic cleansing composition comprising combining at least one anionic surfactant with at least one analgesic composition and a cosmetically suitable carrier to create a mixture, wherein the at least one topical analgesic compound is present at a concentration of 0.01% to 30% by weight, relative to the total weight of the analgesic cleansing composition; wherein the cosmetically suitable carrier comprises at least 50% by weight of one or more alcohols selected from the group consisting of isopropyl alcohol and ethanol based on the total weight of the analgesic cleansing composition;

and homogeneously mixing to create an analgesic cleansing composition; in which the amount of analgesic cleansing composition is sufficient to provide analgesia upon contact with the skin.

14. The method of claim 13, in which the at least one topical analgesic compound comprises a compound selected from *Aleurites moluccanus bakoly* seed oil, aluminum acetate, benzyl alcohol, camphor, capsaicin, *Capsicum frutescens* fruit, *Capsicum frutescens* resin, *Cedrus deodora* wood extract, decursinol, diphenylhydramine, benzocaine, *Ginkgo* leaf terpenoids, hydrocortisone, *Juniperus communis* sprout extract, *Juniperus oxycedrus* wood tar, lauryl PEG-8 dimethicone, lidocaine, *Meconopsis horridula* flower extract, menthol, methyl nicotinate, methyl salicylate, ethyl salicylate, *Ocimum tenuiflorum* oil, *Papaver rhoeas* seed extract, pentafluoropropane, phenol, *Pinus palustris* resin extract, *Piper longum* fruit, *Piper nigrum* fruit, *Piper nigrum* seed, pramocaine, *Saposhnikovia divaricata* root extract, humic acid, turpentine, bendazac, benzyldamine, bufexamac, diethylamine salicylate, etofenamate, felbinac, fepradinol, feprazone, flufenamic acid, ibuprofen, imidazole salicylate, isonixin, ketoprofen, nimesulide, phenylbutazone, piktoprofen, piroxicam, proglumetacin, sadicylamide, salol, salicylic acid, suxibuzone, ufenamate, or salts thereof.

15. The method of claim 14, in which the at least one topical analgesic compound comprises methyl salicylate.

16. The method of claim 13, in which the analgesic cleansing composition further comprises at least one additive selected from a natural polymer, a synthetic polymer, a semi-synthetic polymer, an antibacterial agent, a fragrance, a humectant, a deposition aid, a dye, a pigment, an exfoliant, a conditioning agent, a plant extract, plant matter, an essential oil, an oil, a wax, a silicone oil, a silicone wax, a chelator, a vitamin, a vitamin derivative, an alkali metal halide, and combinations thereof.

\* \* \* \* \*